United States Patent [19]
Tustin et al.

[11] Patent Number: 5,744,637
[45] Date of Patent: Apr. 28, 1998

[54] CARBOXYLIC ACID ACCELERATED FORMATION OF DIESTERS

[75] Inventors: Gerald Charles Tustin; Todd Jay Dickson, both of Kingsport, Tenn.

[73] Assignee: Eastman Chemical Company, Kingsport, Tenn.

[21] Appl. No.: 766,247

[22] Filed: Dec. 13, 1996

[51] Int. Cl.$^6$ ............................ C07C 67/00; C07C 69/34
[52] U.S. Cl. ............................ 560/238; 560/190
[58] Field of Search ........................ 560/238, 190

[56] References Cited

U.S. PATENT DOCUMENTS

| | | | |
|---|---|---|---|
| 2,021,698 | 11/1935 | Perkins | 260/106 |
| 2,859,241 | 11/1958 | Schnizer | 560/238 |
| 3,383,374 | 5/1968 | McTeer | 260/89.1 |
| 3,700,722 | 10/1972 | McTeer | 260/486 |
| 4,337,351 | 6/1982 | Larkins, Jr. | 560/263 |
| 4,843,170 | 6/1989 | Isshiki et al. | 560/261 |
| 4,978,778 | 12/1990 | Isshiki et al. | 560/261 |
| 5,026,903 | 6/1991 | Baker | 560/232 |
| 5,117,046 | 5/1992 | Paulik et al. | 560/232 |
| 5,227,517 | 7/1993 | Waller | 560/238 |

FOREIGN PATENT DOCUMENTS

| | | |
|---|---|---|
| 77116 | 4/1983 | European Pat. Off. . |
| 566370 | 10/1993 | European Pat. Off. . |

OTHER PUBLICATIONS

"Boron Fluoride Catalyzed Addition of Aliphatic Anhydrides to Aldehydes", J. Am. Chem. Soc., 72, 847–8 (1950), Man et al.

"Catalysis by Solid Superacids; 16. Improved Nafion–H Catalyzed Preparation of 1,1–Diacetates from Aldehydes", Synthesis, 962–3 (1982), Olah et al.

"Diacetates From Aldehydes in the Presence of Zeolites", Synthesis, 1077–8 (1995), Pereira et al.

"Aldehydes via Palladium Catalyzed Reductive Carbonylation of Esters", J. Chem. Soc., Chem. Commun. 337–8 (1987) Graff et al.

Chemical Abstracts, 96:34596w, European Patent Appl. EP 34, 062, 19 Aug. 1981.

Chemical Abstracts, 115:28712a, Ger. Offen. DE 3, 934,860, 25 Apr. 91.

Chemical Abstracts, 110: 7679b, Jpn. Kokai Tokkyo Koho Jp. 63, 101, 348, 06 May 1968.

*Primary Examiner*—Paul J. Killos
*Assistant Examiner*—Rosalynd Keys
*Attorney, Agent, or Firm*—Michael J. Blake; Harry J. Gwinnell

[57] ABSTRACT

This invention pertains to accelerating the rate of formation of 1,1-dicarboxylic esters from the reaction of an aldehyde with a carboxylic acid anhydride or a ketene in the presence of a non-iodide containing a strong Bronsted acid catalyst by the addition of a carboxylic acid at about one bar pressure and between about 0° and 80° C. in the substantial absence of a hydrogenation or carbonylation catalyst.

18 Claims, No Drawings

CARBOXYLIC ACID ACCELERATED FORMATION OF DIESTERS

The Government of the United States of America has rights in this invention pursuant to Cooperative Agreement No. DE-FC22-95PC93052 awarded by the U.S. Department of Energy.

BACKGROUND OF THE INVENTION

Diesters having the ester groups attached to the same carbon atom are valuable chemical intermediates. Heating these esters, preferably in the presence of an acid catalyst, produces unsaturated esters. For example, 1,1-ethanediol diacetate, also known as ethylidene diacetate (EDA), can be converted to vinyl acetate and acetic acid by heating at about 140° C. in the presence of a sulfonic acid catalyst. This process has been used commercially. The vinyl acetate product then can be polymerized to produce poly(vinyl acetate). This industrially important polymer and its derivatives are extensively used as adhesives, paints and other coatings, films and laminating materials. EDA itself has also been used to control the growth of bacteria and fungus in crops and animal feeds.

EDA can also be produced by contacting acetylene with acetic acid in the presence of a catalyst, such as a mercury on zinc salt. For example, excellent yields of EDA can be obtained between about 0° and 50° C. by bubbling acetylene through acetic acid containing mercuric sulfate. However, vapor phase operation of that process at 180°–200° C. produces greater amounts of vinyl acetate and lower amounts of EDA, a mode of operation that has been used commercially to produce vinyl acetate. However, the high cost of acetylene and the safety problems associated with its use make this process disadvantageous when compared to ethylene or acetaldehyde-based processes for producing EDA or vinyl acetate.

EDA and vinyl acetate also can be produced by the oxidative acetoxylation of ethylene by contacting oxygen or another oxidizing agent, acetic acid and ethylene in the presence of a palladium catalyst. Operating at temperatures below about 120° C. in acetic acid produces EDA, 1,2-ethanediol diacetate and vinyl acetate and other products. Feeding ethylene, acetic acid and oxygen in this oxidative acetoxylation in the vapor phase at 150°–200° C. at 5–10 bar produces mainly vinyl acetate and water, which process is also used commercially to produce vinyl acetate. However, the explosion hazards associated with this reaction require that the reaction be performed with less than a stoichiometric amount of oxygen, and hence conversions of ethylene, acetic acid and oxygen are typically 10–15%, 15–30% and 60–90% respectively. About 5–10% of the ethylene is converted to carbon dioxide and about 1% is converted to acetaldehyde. The low ethylene and acetic acid conversions per pass require extensive recycling along with a carbon dioxide removal system. Although the capital costs of an ethylene-acetic acid-oxygen-based vinyl acetate plant are high, these are offset by the generally low costs of ethylene and acetic acid. In general, the oxidative acetoxylation of ethylene is not an efficient way to make EDA cleanly.

Numerous attempts have been made to prepare EDA from mixtures of carbon monoxide and hydrogen (synthesis gas) because of very low raw material costs. As initial steps, these schemes convert synthesis gas to methanol or dimethyl ether. In addition, many combinations have been tried utilizing carbonylation of methyl acetate (produced from methanol and recycled acetic acid) or dimethyl ether to produce acetic anhydride. In some schemes, acetic anhydride is partially hydrogenated to produce EDA and acetic acid, but the efficiency of these reactions is generally poor. In other schemes, the methyl acetate or dimethyl ether is carbonylated in the presence of hydrogen to produce EDA and acetic acid in one step, but the product EDA is unstable under the reaction conditions, resulting in tar formation. Other variations on this approach include reacting methanol or methyl acetate with hydrogen and carbon monoxide to produce acetaldehyde and water, or acetaldehyde and acetic acid, respectively. As above, the selectivity to acetaldehyde in these reactions is poor, however. The resulting acetaldehyde is then reacted with acetic anhydride to produce EDA.

Currently, the most efficient way to make EDA is the reaction of acetaldehyde with acetic anhydride in the presence of a Bronsted acid catalyst; heating to about 80° C. is required for the reaction to proceed at a reasonable rate. Unfortunately, the reaction is reversible, and heating the EDA-containing product mixture at elevated temperatures with the catalyst still present can produce acetaldehyde and acetic anhydride. The reversible reaction is illustrated by equation 1:

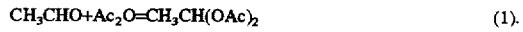

$$CH_3CHO + Ac_2O \rightleftharpoons CH_3CH(OAc)_2 \qquad (1).$$

In addition, however, another equilibrium exists when EDA is heated with the Bronsted acid catalyst still present. That equilibrium produces vinyl acetate and acetic acid from EDA as shown in equation 2:

$$CH_3CH(OAc)_2 \rightleftharpoons CH_2CH(OAc) + HOAc \qquad (2).$$

Both of the equilibria described in equations 1 and 2 favor the formation of EDA. However, since acetaldehyde, acetic anhydride, acetic acid and vinyl acetate are all more volatile than EDA, heating EDA with the Bronsted acid catalyst present decomposes the EDA and volatilizes acetaldehyde, acetic anhydride, acetic acid and vinyl acetate. If the EDA and Bronsted acid catalysts are heated to sufficiently high temperatures (about 140° C.), and excess acetic anhydride is present, the above cracking reactions occur readily causing the equilibria to shift to the production of vinyl acetate and acetic acid by the law of mass action. Although commercial vinyl acetate processes have been based on using the combined chemistry of equations 1 and 2, the process is complicated by the loss of the most volatile component, acetaldehyde, which requires that it must be captured and returned to the reactor. When EDA and acid catalyst are heated under conditions in which the pressure is sufficiently high to prevent volatilizing the volatile components, acetaldehyde and vinyl acetate present undergo other reactions such as aldol condensation and oligomerization to produce tar-like materials. These secondary reactions that occur under pressurized conditions may account for some of the tar-like materials produced in producing EDA from the hydrocarbonylation of methyl acetate or dimethyl ether. Similar difficulties may be encountered when acetic anhydride is hydrogenated under high pressure and acidic conditions.

The equilibria depicted in equations 1 and 2 require that no acid catalyst be present if EDA is to survive heating to temperatures near its normal boiling point, such as during distilling. Thus, because an acid catalyst is required for the formation of EDA, the acid catalyst must be removed before EDA can survive heating without decomposing. If the acid catalyst is a soluble acid, such as the p-toluenesulfonic acid typically used, it must be neutralized. However, neutralizing the acid generates salts, which are environmentally undesirable. The process of the invention allows for the use of lower amounts of sulfonic acid for converting acetaldehyde and acetic anhydride into EDA than the amounts normally used, thus lowering the amount of salt generated at the time of neutralization. The process of the invention also employs much lower temperatures than those normally used in the reaction of acetaldehyde and acetic anhydride, which saves energy. The process of the invention accomplishes these advantages by adding acetic acid to the mixture amplifying the reaction rate, which allows for the use of lower temperature and less catalyst. The process is so facile that it can be used as a means to scrub acetaldehyde out of gas streams very efficiently.

The reason for the rate enhancing effect that results from added acetic acid is not clear. The possible reverse of reaction 2 (formation of EDA from acetic acid and vinyl acetate) does not appear to be contributing significantly to the process of the invention since the reaction of vinyl acetate with acetic acid is slow under the conditions of temperature, Bronsted acid concentration and reactant concentration typically found in the process of this invention. In addition, significant quantities of vinyl acetate normally are not detected at the temperatures used in the process of the invention. Another surprising feature of the invention is that low levels of acetic acid promote the reaction, but this effect ceases before the EDA-forming reaction is completed. However, increasing the level of acetic acid beyond a certain minimum level allows the EDA-forming reaction to be promoted to completion. This type of behavior is not expected with normal catalysts and promoters. Hence, the process of the invention is truly novel and is not predictable from known common organic reactions. Further, if an ultimate goal is to produce vinyl acetate from acetaldehyde and acetic anhydride through the intermediary of EDA, it would be preferable to have no acetic acid present because acetic acid reacts with vinyl acetate in the EDA cracking reaction at high temperature. However, because of the great rate enhancing effect of the acetic acid in the EDA formation process of the invention, it may be advantageous to have some acetic acid present in the EDA used to produce vinyl acetate. The small amount of acetic acid required in the process of the invention is readily removed in the initial stages of the cracking process.

The present invention relates to a process of combining an aldehyde with a carboxylic acid anhydride to produce a diester. In particular, combining acetaldehyde with acetic anhydride to produce EDA. Other processes for producing EDA, such as reacting acetic acid with acetylene or the oxidative acetoxylation of ethylene, will not be discussed in detail here since the reactants involved in those processes are different from those of the present invention. Skirrow et al. in U.S. Pat. No. 1,638,713 and by Dykstra in U.S. Pat. No. 1,849,616 describe production of EDA from acetylene and acetic acid. British Patent No. 1,124,862 describes production of EDA from oxidative acetoxylation of ethylene. These chemistries can be modified to produce vinyl acetate, and an overview of these modified processes is provided by Daniels in *Kirk-Othmer Encyclopedia of Chemical Technology*, 3rd ed., Howe-Grant, M. Ed., Wiley Interscience: New York, 1983, Vol. 23 pp. 820–824.

The acid-catalyzed reaction of acetic anhydride with acetaldehyde is an excellent way to produce EDA. Perkins, in U.S. Pat. No. 2,021,698, describes the reaction of acetic anhydride with acetaldehyde (fed as paraldehyde) in the presence of sulfuric, toluene-sulfonic or phosphoric acid catalysts at boiling temperatures to produce vinyl acetate through the intermediary EDA. Schnizer, in U.S. Pat. No.

2,859,241, describes a process for producing 1,1-dicarboxylates, including EDA, by reacting carboxylic anhydride with an aldehyde in the presence of an arenesulfonic acid. McTeer, in U.S. Pat. Nos. 3,700,722 and 3,383,374, describes the reaction of acetic anhydride and excess acetaldehyde at 25°–100° C. (preferably 40°–60° C.) in the presence of sulfuric acid to produce a mixture of EDA and bis(1-acetoxyethyl) ether after neutralizing the reaction with sodium hydroxide. Man et al., in *J. Am. Chem. Soc.* 72, 847–8 (1950), describe the use of a Lewis acid, $BF_3$ etherate, as a catalyst for the reaction of aliphatic anhydrides with aliphatic and aromatic aldehydes to produce 1,1-dicarboxylates. Olah, in *Synthesis* 962–3 (1982), describes the use of the polymeric sulfonic acid, Nafion®-H, as a catalyst for producing 1,1-diacetates from aldehydes and acetic anhydride. Pereira, in *Synthesis* 1077–8 (1995), describes the use of zeolite HY as a catalyst for the synthesis of 1,1-diacetates from the reaction of acetic anhydride with aldehydes in carbon tetrachloride solvent. None of the processes described above uses acetic or other carboxylic acid as a rate-enhancing promoter component as in the present invention.

Isshiki, in U.S. Pat. No. 4,843,170, describes a process of reacting a mixture of acetaldehyde and dimethylacetal produced by a hydrocarbonylation reaction with acetic anhydride in the presence of benzenesulfonic acid, or other Bronsted or Lewis acids, to produce a mixture of EDA and methyl acetate. The methyl acetate is then converted to acetic anhydride by carbonylation. The EDA-producing portion of this scheme is different from the above described EDA-producing schemes in that methyl acetate is co-produced, but otherwise offers no advantage in the actual production of EDA. The rate-enhancing addition of acetic acid of the present invention is not used in the process of U.S. Pat. No. 4,843,170.

Several processes have been disclosed in which EDA is produced by the hydrogenation of acetic anhydride. For example, Isshiki, in U.S. Pat. No. 4,978,778, describes a process for the production of vinyl acetate and acetic acid by reacting acetic anhydride with hydrogen in the presence of a metal belonging to Group VIII (current I.U.P.A.C. notation is Groups 8, 9 and 10) of the Periodic Table and an acidic substance or a halide. In addition to vinyl acetate and acetic acid, the process of U.S. Pat. No. 4,978,788 produces considerable amounts of EDA and some acetaldehyde. Isshiki, in European Patent Application EP 34,062, describes a process for producing EDA and small amounts of acetaldehyde, ethyl acetate, methyl acetate and acetic acid from the reaction of acetic anhydride and hydrogen in the presence of a metal belonging to Group VIII of the Periodic Table, a halide and an amine. Larkins, in U.S. Pat. No. 4,337,351, describes the production of EDA from the reaction of acetic anhydride with hydrogen in the presence of methyl iodide and a Ru catalyst. All of these hydrogenation reactions suffer from the complications that result from heating acid catalysts in the presence of EDA: production of confined acetaldehyde and vinyl acetate, which undergo subsequent reactions to produce tars. In addition, systems containing halide, such as U.S. Pat. No. 4,337,351, are corrosive and produce halogen-containing byproducts. Systems containing sulfonic acid undergo partial reduction of the sulfonic acid to low valent sulfur species that poison the hydrogenation catalyst, which causes them to lose their effectiveness as acid catalysts. Okada et al., in Japanese Kokai Tokkyo Koho JP 63,101,348, describe a non-corrosive catalyst, Ni, Fe or Co, for the hydrogenation of acetic anhydride to EDA at high temperature (400° C.). The selectivity of this reaction (36.5%) is poor when the reaction is run at a modest conversion (68.7%). The acetic anhydride hydrogenation reactions described above produce acetic acid as a reaction product, but acetic acid is not present at the start of the reaction; by contrast, the process of the present invention has acetic acid present at the start of the reaction, which is neither produced or consumed. In addition, the temperatures and pressures of the acetic anhydride hydrogenation reactions are much higher than those required for the present invention. Further, the process of the invention is performed in the substantial absence of hydrogenation catalysts since these catalysts will reduce the strong acid catalysts of the invention in the presence of hydrogen. An advantage of the present invention lies in the low temperature and low pressure mode of operation it employs.

Others have described production of EDA by carbonylation or hydrocarbonylation reactions in the presence of iodide and a Group VIII metal catalyst. Some of these processes exclude acetic acid at the start of the reaction. Baker, in U.S. Pat. No. 5,026,903, describes a process whereby dimethyl acetal is reacted with carbon monoxide in the presence of methyl acetate, Rh, LiI and an optional ligand to produce a mixture containing EDA, methyl acetate and acetic anhydride. Lindner et al., in Ger. Offen. DE 3,934,860, describe a process in which methyl acetate is reacted with hydrogen and carbon monoxide at elevated temperature and pressure in the presence of a catalyst containing Rh and an ether phosphine ligand plus a Pd or Ru co-catalyst and an alkali or alkali earth iodide to produce EDA and a stoichiometric amount of acetic acid along with small amounts of acetaldehyde, ethyl acetate, and vinyl acetate. Graff et al., in *J. Chem. Soc., Chem. Commun.* 337–8 (1987), describe a process in which methyl acetate is reacted with hydrogen and carbon monoxide in the presence of palladium catalysts and quaternary iodide salts in acetophenone to produce a mixture containing acetaldehyde, acetic acid, acetone and EDA. Several of the processes for forming EDA by carbonylation or hydrocarbonylation reactions in the presence of iodide and a Group VIII metal catalyst include systems containing acetic acid at the start of the reaction. Studer et al., in European Patent Application EP 566,370, describe a process of reacting a mixture of dimethyl ether, methanol, water and acetic acid in the presence of a catalyst system containing a Group VIII metal, methyl iodide, lithium iodide and optional lithium acetate to produce products including EDA, acetic acid, acetic anhydride and methyl acetate. Paulik et al., in U.S. Pat. No. 5,117,046, describe a process whereby dimethyl ether and/or methyl acetate are reacted with carbon monoxide and hydrogen in the presence of acetic anhydride, acetic acid, Rh, Pd, methyl iodide and lithium acetate to produce a product mixture containing methyl acetate, acetic anhydride and EDA. Paulik et al., in European Patent Application EP 77,116, describe a process whereby methyl acetate is reacted with carbon monoxide and hydrogen in the presence of acetic anhydride, small amounts of acetic acid, Rh, Pd, methyl iodide, a tertiary P, As, N, or Sb ligand or lithium acetate to produce a product mixture containing EDA. All of these carbonylation or hydrocarbonylation reactions suffer from the complications resulting from heating acid catalysts in the presence of EDA: EDA cracking reactions produce confined acetaldehyde and vinyl acetate which undergo subsequent reactions to produce tars. Further systems containing halide are corrosive and also produce halogen-containing byproducts.

Waller, in U.S. Pat. No. 5,227,517, describes the reaction of acetaldehyde with acetic anhydride in the presence of acetic acid and an iodide source to produce a product mixture containing EDA. The rate of the reaction is enhanced by the use of the acetic acid solvent. Suitable iodide sources are lithium iodide, potassium iodide and methyl iodide. Surprisingly, iodide in the form of the Bronsted acid HI is not a suitable catalyst for the reaction. In view of the teaching of U.S. Pat. No. 5,227,517 regarding the unsuitability of the Bronsted acid HI, it is surprising that Bronsted acids of the sulfonic acid type work so well in the presence of acetic acid in the process of the present invention.

Unlike previous processes, the present invention accelerates the rate of formation of 1,1-dicarboxylic esters from the reaction of an aldehyde with a carboxylic acid anhydride or a ketene in the presence of a non-iodide containing Bronsted acid catalyst by adding a carboxylic acid at about one bar pressure and between about 0° and 80° C. in the substantial absence of a hydrogenation catalyst or a carbonylation catalyst. The substantial absence of iodine-containing species decreases the corrosiveness of the process, and no organic iodide byproducts are formed. The substantial absence of hydrogenation catalysts allows for extended strong acid catalyst lifetime should any hydrogen be present, and allows for less expensive equipment since typical high pressure hydrogenation conditions are not required in the process of the invention. The substantial absence of carbonylation catalyst components (typically Rh or Ni and methyl iodide) allows the process of the invention to produce a purer product without the expense and operational complications associated with handling and recovering carbonylation catalyst components. Because the process of the present invention operates at low pressure and temperature, the complications resulting from prolonged heating of acid catalysts in the presence of a 1,1-dicarboxylic ester are avoided. In the case of EDA, the EDA cracking reactions that produce confined acetaldehyde and vinyl acetate which undergo subsequent reactions to produce tars at high temperature no longer are significant at low temperature.

SUMMARY OF THE INVENTION

This invention relates to an improved processes for producing 1,1-dicarboxylic esters, the process of the invention employs a carboxylic acid as a promoter. In addition, the invention uses a non-iodiode containing Bronsted acid under mild conditions, which provides a less corrosive process and no organic iodide-containing byproducts. Further advantages of the present invention are both set forth above and exemplified and explained in detail below.

This invention relates to a process for accelerating the rate of forming 1,1-dicarboxylic esters. The dicarboxylic esters are formed by reacting an aldehyde with a carboxylic acid anhydride or a ketene in the presence of a non-iodide containing strong Bronsted acid catalyst and in the substantial absence of a hydrogenation catalyst or a carbonylation catalyst by adding a carboxylic acid at about one bar pressure and between about 0° and about 80° C.

In particular, the invention relates to a process for producing 1,1-dicarboxylic esters comprising the steps of: 1) contacting an aldehyde of the formula $R^4CHO$, a carboxylic acid anhydride of the formula $(R^1CO)O(OCR^2)$ or a ketene, and a carboxylic acid of the formula $R^3COOH$ in the presence of non-iodide containing strong Bronsted acid and the substantial absence of either a hydrogenation catalyst or a carbonylation catalyst in a contact zone; and 2) recovering the 1,1-dicarboxylic ester from the contact zone. In the above formula, $R^1$, $R^2$ and $R^3$ are each alkyl and are identical or different and contain 1–10 carbon atoms; $R^4$ is hydrogen or is an alkyl containing 0 to 10 carbon atoms; and if a ketene is used instead of a carboxylic acid anhydride, the ketene should be selected such that it has the same number of carbon atoms as the carboxylic acid promoter.

DETAILED DESCRIPTION OF THE INVENTION

An object of the present invention is to provide a more efficient process for the formation of 1,1-diesters by reacting an aldehyde with a carboxylic acid anhydride or ketene in the presence of a non-iodine containing strong Bronsted acid catalyst and a carboxylic acid and in the absence of hydrogenation or carbonylation catalysts. The process of the invention is performed within a contact zone wherein the carboxylic acid, carboxylic acid anhydride or ketene, acetaldehyde and a strong acid catalyst are contacted. The carboxylic acid anhydride ($R^1CO)O(OCR^2$) may be such that $R^1$ is identical to $R^2$ or different; $R^1$ and $R^2$ are each alkyl and contain about 1–10 carbon atoms. Preferably $R^1$ and $R^2$ are identical and contain 1–6 carbons. More preferably the carboxylic acid anhydride is acetic, propionic or butyric anhydride. The most preferred carboxylic acid anhydride is acetic anhydride. The carboxylic acid $R^3COOH$ is such that $R^3$ is an alkyl of 1–10 carbon atoms; $R^3$ may be the same or different from $R^1$ and $R^2$. Preferably $R^3$, $R^1$ and $R^2$ are identical and contain 1–6 carbon atoms. More preferably the carboxylic acid is acetic, propionic or butyric acid. The most preferred acid is acetic acid. The aldehyde $R^4CHO$ may be such that $R^4$ is hydrogen of an alkyl of about 0–10 carbon atoms. Preferably $R^4$ is an alkyl of 1–6 carbon atoms. More preferably the aldehyde is acetaldehyde, propionaldehyde or butyraldehyde. The most preferred aldehyde is acetaldehyde. If a ketene is used instead of the carboxylic acid anhydride, it should be chosen so that the product of its reaction with carboxylic acid $R^3COOH$ would yield the carboxylic acid anhydride ($R^1CO)O(OCR^2$), and, in this case, $R^3$ would be the same as $R^1$ which would be the same as $R^2$.

For the preparation of EDA from acetic anhydride and acetaldehyde, the acetic anhydride may be produced by essentially any practical means, such as by carbonylating methyl acetate or dimethyl ether or by reacting ketene with acetic acid. Since the process of the invention contains a carboxylic acid, some or all of the carboxylic anhydride can be replaced by a ketene. The reaction of the ketene with a portion of the carboxylic acid charged will generate the carboxylic anhydride required for the process of the invention. The acetaldehyde used for the preparation of ethylidene dicarboxylates may be produced by any route, such as via the Wacker process, ethanol dehydrogenation, the hydrocarbonylation of methyl acetate or methanol, or the by hydrogenation of acetic acid, acetic anhydride or ketene. In one embodiment, ketene is used as a source of both the acetaldehyde (from the hydrogenation of ketene) and acetic anhydride for the preparation of EDA. Any common source of acetic acid can be used in the process of the invention provided the acetic acid is not contaminated with components that react with either the reactants or products.

The contact zone can contain a strong acid catalyst in a liquid solution or as a mixture of solid acid and liquid. The preferred strong acid should be a Bronsted acid. More preferred strong acids are those containing phosphorous or sulfur in a positive oxidation state, which include the liquid phosphoric, sulfuric and methanesulfonic acids, the soluble solid benzenesulfonic, p-toluenesulfonic, naphthalene-sulfonic and naphthalenedisulfonic acids and insoluble acidic ion exchange resins, such as Amberlyst® 15 and Nafion® 117 polymeric sulfonic acids. Most preferred strong acids are sulfuric, methanesulfonic, benzenesulfonic, p-toluenesulfonic, naphthalenesulfonic and naphthalenedisulfonic acids, Amberlyst® 15 and Nafion® polymeric sulfonic acid. Hydrohalic acids, especially hydriodic acid, are not well suited for the process of the invention.

The concentration of the strong acid should range from about 0.001 to about 2.0 acid equivalents per liter of solution. The process of the invention is possible with acid concentrations outside this range, but excessively dilute acid concentrations tend to provide lower rates, and excessively high acid concentrations are wasteful since one of the objectives of the invention is to reduce the amount of strong acid required. In general, the amount of strong acid required decreases as the strength of the acid increases and as the temperature increases. The optimal concentration range can also depend on the identity of the carboxylic acid, carboxylic acid anhydride and aldehyde reaction. When the carboxylic acid is acetic acid and the reactants are acetic anhydride and acetaldehyde, and the strong acid is benzenesulfonic acid, and the reaction is performed at less than 50° C., then concentrations ranging between 0.003 and 0.2 molar are satisfactory. The most preferred range for these specific reactants and strong acid catalysts is between about 0.01 and about 0.12 molar. Lower concentrations of strong acid are desirable if the mixture containing the 1,1-dicarboxylic ester is to be neutralized by the addition of a base so that the 1,1-dicarboxylic ester can be isolated and purified. Higher concentrations of strong acid are desirable if the same strong acid catalyst is to be used in cracking the 1,1-dicarboxylic ester to an unsaturated ester such as in the conversion of EDA to vinyl acetate.

The molar ratio of carboxylic acid anhydride to aldehyde is not critical and can range from about 0.05 to about 20. Excessive amounts of aldehyde can produce byproducts such as di(1-acyloxyaliphatic) ethers in some cases, and can require the use of elevated pressures if the aldehyde is volatile such as in the case of acetaldehyde. A more preferred ratio of carboxylic acid anhydride to aldehyde is from about 0.1 to 10 and the most preferred ratio of carboxylic acid anhydride to aldehyde is from about 0.4 to about 8. If the 1,1-dicarboxylic ester is EDA, and it is subsequently desired to convert the EDA-containing mixture to vinyl acetate, then the ratio of carboxylic acid anhydride to aldehyde should be greater than 1. If a ketene is used as a replacement for all or a portion of the carboxylic acid anhydride, the ketene to aldehyde molar ratios are the same as above, but sufficient carboxylic acid promoter should be present to convert the ketene to the carboxylic acid anhydride and to still have enough carboxylic acid remaining to promote the reaction accelerating feature of the invention after all of the ketene is consumed.

The amount of carboxylic acid required to promote to process of the invention is very small, but it also can be present in sufficiently large amounts as to be the main component of the mixture. In one example of the invention, a mixture of carboxylic acid and strong acid catalyst can be used as a solvent to convert a continuous feed of ketene or carboxylic acid anhydride and the aldehyde into the 1,1-dicarboxylic ester under very mild conditions of about one atmosphere pressure and at ambient temperature. Thus 0.12 molar benzenesulfonic acid in acetic acid is an efficient scrubber medium for the removal of ketene and acetaldehyde from gas streams at ambient temperature and pressure, and EDA is produced in the scrubber solution. The minimum amount of carboxylic acid required can depend on the identity and relative amounts of the carboxylic acid, the carboxylic acid anhydride or ketene, the aldehyde, the strong acid catalyst and the temperature. In the case of acetic anhydride, acetaldehyde, benzenesulfonic acid and acetic acid, when the molar ratio of acetic anhydride to acetaldehyde to benzenesulfonic acid to acetic acid=1.0/0.12/0.0014/0.0087, an initial rate enhancement is observed, and the reaction reaches about 16% conversion to EDA in 5 minutes at room temperature. However, the rate enhancement effect then ceases after 16% conversion is reached at these low acetic acid levels, and the reaction only proceeds to about 29% conversion to EDA after an additional 300 minutes. When the amount of acetic acid is increased so that the above ratio=1.0/0.12/0.0014/0.088, the rate enhancement effect is greater and the reaction proceeds to about 46% conversion to EDA in 5 minutes. However, the rate enhancement effect diminishes after about 46% conversion is reached, but the reaction is essentially complete after an additional 60 minutes. When the amount of acetic acid is increased further so that the above ratio=1.0/0.12/0.0014/0.18, the reaction was essentially completed in about 10 minutes, and the rate enhancement effect is operational throughout the entire course of the reaction. Thus, in the case of EDA formation, the rate enhancement effect is observable when the moles of acetic acid are considerably less than the moles of acetaldehyde, but the effect diminishes as conversion proceeds. When the level of acetic acid is comparable to that of acetaldehyde, the rate enhancement effect continues throughout the entire course of the reaction. In the cases where minimal levels of acetic acid is used, the solvent of the reaction is acetic anhydride. The intermediate case, where acetic anhydride, acetaldehyde and acetic acid are mixed in approximately equal molar amounts at room temperature, is very efficient and can become exothermic at 0.08 molar benzenesulfonic acid levels. Under the same conditions where the acetic acid is omitted, very little reaction occurs in a reasonable time period. Thus, the molar ratio of aldehyde to carboxylic acid promoter is about 10 to 1 or less; the preferred ratio is about 1 to 1.

The temperature of the reaction can range from about −20° to about 200° C. A more preferred range is from about 0° to about 160° C. However, at high temperature, cracking of the 1,1-dicarboxylic ester can occur producing unsaturated esters. In some cases, high temperature operation will require higher pressures to keep the reactants within the contact zone. If the reactants and products are confined at high temperature and pressure for an extended time, resinous byproducts can be produced thus decreasing the yield and purity of the desired 1,1-dicarboxylic ester. More preferred temperatures for the process of the invention are from about 0° to about 80° C. Most preferred temperatures range from about 20° to about 50° C. The reaction is exothermic, and the temperature can be maintained in the desired region by common methods of heat exchange practiced by those experienced in the art, along with controlling the rate of addition of reactants and adjusting the amounts of carboxylic acid promoter and strong acid catalyst.

The pressure of the reaction is not critical, provided there is sufficient pressure to keep the reactants in the contact zone for the desired degree of reaction. Typical operating pressure is about 1 to about 10 bar absolute. Operating pressures outside this range are within the scope of the invention, but there generally is no advantage to using excessively high or low pressure. If the temperature is sufficiently high to require elevated pressure, then the risk of forming resinous byproducts increases. An advantage of the present invention is the savings it offers in energy and equipment costs resulting from low temperature and low pressure operating conditions. The process of the invention can be operated in the presence of diluent gases, but the gases and the conditions should be such that the gases do not react with the reactants, products or strong Bronsted acid catalyst. Thus, hydrogen can be present as a diluent gas, but a hydrogenation catalyst should be absent to prevent reduction of the Bronsted acid catalyst. In a particular embodiment, acetaldehyde, which has been formed from the hydrogenation of ketene in a separate contact zone over a heterogeneous catalyst, and ketene and hydrogen are fed to a contact zone containing acetic acid, optional acetic anhydride, and a strong Bronsted acid catalyst to remove the acetaldehyde and ketene as EDA. Carbon monoxide may be present as a diluent gas, but the typical rhodium or nickel and iodine-containing species normally present in a typical carbonylation reaction mixtures should be substantially absent from the contact zone to minimize the production of iodine-containing byproducts. Other diluent gases acceptable for the process of the invention include nitrogen, inert gases such as helium or argon, and hydrocarbons such as methane or ethane. Molecular oxygen-containing gases, such as air, can be present in the process of the invention, but they are not preferred owing to the possibility of ignition. Diluent gases can comprise about 0 to about 95 mole % of the mixture present in the contact zone.

The following examples are presented to illustrate the present invention, but are not intended in any way to limit the scope of the invention.

EXAMPLES

Example 1

This example illustrates the process of the invention conducted in acetic acid present in a 78 molar % excess over equal molar amounts of acetaldehyde and acetic acid. Acetic acid (36.4 g), acetic anhydride (36.75 g) and benzenesulfonic acid monohydrate (1.27 g) were charged into a bottle and stirred magnetically at ambient temperature (about 20°–23° C.). Acetaldehyde (15.9 g), cooled to about 0° C., was added to the stirred mixture. After stirring for 20 minutes, the temperature of the mixture was 50° C. About two hours after initially mixing the reagents, the mixture was analyzed by gas chromatography using Hewlett Packard Model 5890 gas chromatographs using flame ionization detectors. Vinyl acetate, acetaldehyde, paraldehyde and acetic acid were analyzed using a 25 m×0.53 mm FFAP capillary column (1.0 micron film thickness) programmed at 40° C. for 5 minutes, 15° C./minute to 235° C. and holding at 235° C. for 1.67 minutes. Acetic anhydride and ethylidene diacetate were analyzed using a 30 m×0.53 mm DB-5 capillary column (1.5 micron film thickness) programmed at 40° C. for 8 minutes, 7° C./minute to 200° C. with a 0 minute holding time at 200° C. Analyses were accurate to within about 5%. Mixtures were prepared for gas chromatographic analysis by adding 5 mL of a tetra-hydrofuran solution containing 2% decane internal standard to an accurately weighed 1 g sample of the reaction product. The mixture analyzed as containing 1.9 wt. % acetaldehyde, 0 wt % paraldehyde, 43.8 wt % acetic acid, 11.8 wt % acetic anhydride, 0 wt % vinyl acetate and 46.0 wt % EDA.

Example 2 (Comparative)

This example illustrates the effect of omitting the acetic acid promoter and using additional acetic anhydride to allow for the concentration of acetaldehyde and benzenesulfonic acid to comparable to those used in Example 1. Acetic anhydride (65.2 g) and benzenesulfonic acid monohydrate (1.27 g) were charged into a bottle and stirred magnetically at ambient temperature (about 20°–23° C.). Acetaldehyde (15.9 g), cooled to about 0° C., was added to the stirred mixture. After stirring for 20 minutes, the temperature of the mixture was 26° C. About three hours after initially mixing the reagents, the mixture was analyzed by gas chromatography as per Example 1. The mixture analyzed as containing 14.3 wt % acetaldehyde, 1.6 wt % paraldehyde, 85.2 wt % acetic anhydride and 2.1 wt % EDA.

Examples 3–5

Examples 3–5 used the following instrument to analyze the reaction. The ReactIR® 1000 by Applied Systems is a compact bench top instrument designed for real-time, in-situ analysis of chemical reactions. The ReactIR® 1000 is based on mid-infrared Fourier transform spectroscopy, and is typically used to identify and track the concentration of starting materials, intermediates, and products, thereby providing both reaction pathway and kinetics information. The DiComp probe is a very rugged probe that will with stand many corrosive chemical environments. It has a six-reflection bi-layer ATR element with a temperature range of −80° to 230° C. The pressure range for the DiComp probe is 10 torr to 200 psig. The probe has a wavelength range from 4000 $cm^{-1}$ to 2200 $cm^{-1}$ and from 1900 $cm^{-1}$ to 700 $cm^{-1}$. The probe has a sliding 24/40 ground glass joint on it so it can be used on various sizes of reaction flasks and at various depths. Spectra were collected at 4 $cm^{-1}$ resolution and 32 scans were co-added.

Example 3

This example illustrates the process of the invention performed at a level of acetic acid promoter sufficient to induce an initial rate enhancement but at too low a level to promote the reaction to completion. Acetic anhydride (200 g), acetic acid (1.0 g) and benzenesulfonic acid monohydrate (0.5 g) were charged into a 500 mL 2-necked bottle and stirred magnetically. The DiComp probe was inserted into the reaction mixture through one of the necks of the 500 mL 2-necked bottle while the mixture stirred magnetically at ambient temperature. Acetaldehyde (10.3 g) was added to the stirred mixture as rapidly as possible, and the absorbance of the infrared absorption uniquely characteristic of EDA occurring at 951.3 $cm^{-1}$ was monitored by recording the spectrum every 60 seconds. Relevant absorbance data as a function of time follow.

| Time after acetaldehyde addition, sec. | absorbance |
| --- | --- |
| 0 | 0.0007 |
| 60 | 0.0267 |
| 120 | 0.0426 |
| 180 | 0.0472 |
| 240 | 0.0534 |
| 600 | 0.0553 |
| 1200 | 0.0566 |
| 2400 | 0.0587 |
| 4200 | 0.0635 |

At the concentrations used in the example, the absorbance at equilibrium conversion of the acetaldehyde to EDA is about 0.32–0.34

Example 4

This example illustrates the process of the invention performed at a level of acetic acid promoter higher than that used in Example 3, the level being sufficient to induce an initial rate enhancement followed by a lesser extent of promotion the reaction all the way to completion. Acetic anhydride (200 g), acetic acid (10.3 g) and benzenesulfonic acid monohydrate (0.5 g) were charged into a 500 mL 2-necked bottle and stirred magnetically. The reaction was initiated by adding acetaldehyde (10.3 g) as rapidly as possible, and the reaction was monitored as per Example 3 except that the spectra were recorded every 45 seconds. In the data that follow below, the acetaldehyde was added between 45 and 90 seconds after the spectrophotometer began recording spectra.

| Time after recording the first spectrum, sec. | absorbance |
| --- | --- |
| 0 | 0.0019 |
| 45 | −0.003 |
| 90 | 0.0980 |
| 135 | 0.1558 |
| 180 | 0.1656 |
| 360 | 0.1777 |
| 720 | 0.1898 |
| 1500 | 0.2426 |
| 3900 | 0.3214 |

At the concentrations used in the example, the absorbance at equilibrium conversion of the acetaldehyde to EDA is about 0.32–0.34.

Example 5

This example illustrates the process of the invention performed at a level of acetic acid promoter higher than that used in Example 4, the level being sufficient to induce a rate enhancement that persists unabated throughout the entire course of the reaction. Acetic anhydride (200 g), acetic acid (20.3 g) and benzenesulfonic acid monohydrate (0.5 g) were charged into a 500 mL 2-necked bottle and stirred magnetically. The reaction was initiated by adding acetaldehyde (10.3 g) as rapidly as possible, and the reaction was monitored as per Examples 3 and 4, and the spectra were recorded every 45 seconds. In the data that follow below, the acetaldehyde was added between 45 and 90 seconds after the spectrophotometer began recording spectra.

| Time after recording the first spectrum, sec. | absorbance |
| --- | --- |
| 0 | 0.0004 |
| 45 | 0.0016 |
| 90 | 0.1445 |
| 135 | 0.2234 |
| 180 | 0.2375 |
| 360 | 0.2786 |
| 720 | 0.3018 |
| 1500 | 0.3089 |
| 3900 | 0.3190 |

At the concentrations used in the example, the absorbance at equilibrium conversion of the acetaldehyde to EDA is about 0.32–0.34.

Example 6

This example illustrates the use of the process of the invention as a means to scrub diluted ketene and acetaldehyde from a gas stream forming EDA by contacting the gas with acetic acid containing benzenesulfonic acid catalyst. The scrubber system consisted of four major parts: a scrubber reservoir, a pumping system to circulate liquid from the scrubber reservoir to the top of the scrubber column, an adapter to disperse the liquid from the pumping system outlet into the top of the scrubber column and the scrubber column. The scrubber reservoir was a modified 100 mL long-necked flask fitted with a gas inlet line angled into the neck at 45 degrees, a dip tube extending through the wall of the flask down almost to the base of the flask and a stopcock at the base of the flask. The pumping system consisted of a Masterflex® peristaltic pump with PharMed® tubing to transport the liquid from the reservoir via the dip tube through the pump to the adapter at the top of the scrubber column. The adapter at the top of the scrubber column allowed the liquid to enter the side of the adapter and to be dispersed downward from the center of the adapter while allowing gas to exit from the top of the scrubber column. The scrubber column was a 19 mm I.D. by 900 mm long Hempel distillation column loaded with 6 mm O.D. by 6 mm long Raschig rings. The scrubber reservoir was attached to the base of the scrubber column. The scrubber reservoir was loaded with a solution of acetic acid (60 mL) containing benzenesulfonic acid monohydrate (1.29 g), and this mixture was circulated through the scrubber system. Nitrogen gas metering was provided by Tylan Model FC-260 mass flow controllers. Ketene was generated by the method described by Fisher et al. in *J. Org. Chem.*, 18, 1055–1057 (1953) by the pyrolysis of acetic anhydride and collected in a trap vaporizer assembly at −78° C. The ketene trap/vaporizer assembly was a modified two-piece 32×200 mm vacuum trap having the bottom portion of the trap narrowed to 19 mm O.D. and extending an additional 100 mm. A 7 mm O.D./2 mm I.D. gas inlet tube extended along the outer body of the ketene trap/vaporizer assembly and was connected to the base of the extended tube section. The gas inlet tube was connected to a metered nitrogen line. The ketene inlet line was the normal inside 10 mm O.D. tube found in the standard vacuum trap design. The ketene trap/vaporizer outlet line was the normal 10 mm O.D. side tube found in the standard vacuum trap design. The raw ketene entered the trap/vaporizer assembly through the ketene inlet line where it was condensed. To meter the ketene, nitrogen was fed to the ketene trap/vaporizer gas inlet tube at 88 SCCM (standard cubic centimeters per minute) at −78° C. The nitrogen/ketene mixture then exited the trap/vaporizer assembly through the trap/vaporizer outlet line. Ketene feed rate was 0.7 mmol/minute under these conditions. A similar trap/vaporizer assembly, held at −20° C. and containing freshly distilled acetaldehyde, was used to provide a nitrogen/acetaldehyde mixture by metering nitrogen at 118 SCCM through the chilled acetaldehyde. Acetaldehyde feed rate was 1.0 mmol/minute under these conditions. The nitrogen/ketene and nitrogen/acetaldehyde streams were combined and mixed with an additional nitrogen stream metered at 25 SCCM. The combined nitrogen/ketene/acetaldehyde stream was fed to the inlet line of the scrubber reservoir for six hours while the scrubber fluid circulated. The fluid was then drained from the scrubber reservoir and analyzed by gas chromatography as per Example 1. The scrubber fluid analyzed as containing 2.9 wt % acetaldehyde, 0.1 wt % paraldehyde, 54.1 wt % acetic acid, 0 wt % acetic anhydride and 44.5 wt % EDA.

We claim:

1. A process for producing 1,1-dicarboxylic esters comprising the steps of:

1) contacting a carboxylic acid anhydride of the formula $(R^1CO)O(OCR^2)$ or a ketene, a carboxylic acid promoter of the formula $R^3COOH$, and an aldehyde of the formula $R^4CHO$, wherein the molar ratio of aldehyde to carboxylic acid promoter is about 10 to 1, at a temperature of about 0° to about 80° C., in the presence of a non-iodide containing strong Bronsted acid catalyst in a contact zone that is substantially free of a hydrogenation catalyst or a carbonylation catalyst, wherein $R^1$ and $R^2$ are identical and are an alkyl having 1 to 10 carbon atoms, $R^3$ is an alkyl that is the same as or different from $R^1$ or $R^2$ and contains 1–10 carbon atoms, and $R^4$ is hydrogen or an alkyl of 0 to 10 carbon atoms; and 2) recovering a product comprising the 1,1-dicarboxylic ester.

2. A process according to claim 1 wherein $R^1$, $R^2$ and $R^3$ are identical and contain 1–6 carbon atoms and $R^4$ is the same as or different from $R^1$–$R^3$ and contains 1–6 carbon atoms.

3. A process according to claim 2 wherein the carboxylic acid anhydride is acetic, propionic or butyric anhydride; the carboxylic acid promoter is acetic, propionic or butyric acid; the aldehyde is acetaldehyde, propionaldehyde, or butyraldehyde; and the molar ratio of aldehyde to carboxylic acid promoter is about 1 to 1.

4. A process according to claim 3, wherein the carboxylic acid anhydride is acetic anhydride, the carboxylic acid is acetic acid and the aldehyde is acetaldehyde.

5. A process according to claim 1 wherein a ketene is contacted instead of a carboxylic acid anhydride, said ketene having the same number of carbon atoms as the carboxylic acid.

6. A process according to claim 1 wherein the contacting is at a pressure of about 1 to about 10 bars absolute.

7. A process according to claim 6 wherein the temperature is about 20° to about 50° C.

8. A process according to claim 1 wherein a diluent gas is also fed into the contact zone.

9. A process according to claim 1 wherein the Bronsted acid catalyst is selected from the group consisting of phosphoric acid, sulfuric acid, methanesulfonic acid, benzenesulfonic acid, p-toluenesulfonic acid, naphthalenesulfonic acid, naphthalenedisulfonic acid and an insoluble acidic ion exchange resin.

10. A process according to claim 4 wherein the product recovered from the contact zone comprises ethylidene diacetate.

11. A continuous process for the production of 1,1-dicarboxylic esters comprising the steps of:

1) continuously feeding a carboxylic acid anhydride of the formula $(R^1CO)O(OCR^2)$ or a ketene, a carboxylic acid promoter of the formula $R^3COOH$, an aldehyde of the formula $R^4CHO$ and, optionally, a non-reactive diluent gas into a contact zone containing a strong Bronsted acid catalyst, wherein the molar ratio of aldehyde to carboxylic acid promoter is about 10 to 1, at a temperature of about 0° to about 80° C. and at a pressure of about 1 to about 10 bars absolute, provided that the contact zone is substantially free of a hydrogenation catalyst or a carbonylation catalyst, wherein $R^1$ and $R^2$ are identical and are an alkyl of 1 to 10 carbon atoms and $R^3$ is an alkyl that is the same or different from $R^1$ and $R^2$ and contain 1 to 10 carbon atoms, and $R^4$ is hydrogen or an alkyl of 0 to 10 carbon atoms; and 2) continuously removing a product comprising the 1,1-dicarboxylic ester from the contact zone.

12. A continuous process according to claim 11 wherein $R^1$, $R^2$ and $R^3$ are identical and contain 1–6 carbon atoms and $R^4$ is the same as or different from $R^1$–$R^3$ and contains 1–6 carbon atoms.

13. A continuous process according to claim 12 wherein the carboxylic acid anhydride is acetic, propionic or butyric anhydride; the carboxylic acid promoter is acetic, propionic or butyric acid; the aldehyde is acetaldehyde, propionaldehyde, or butyraldehyde; and the molar ratio of aldehyde to carboxylic acid promoter is about 1 to 1.

14. A continuous process according to claim 13, wherein the carboxylic acid anhydride is acetic anhydride, the carboxylic acid is acetic acid and the aldehyde is acetaldehyde.

15. A continuous process according to claim 11 wherein a ketene is contacted instead of a carboxylic acid anhydride, said ketene having the same number of carbon atoms as the carboxylic acid.

16. A continuous process according to claim 11 wherein the temperature is about 20° to about 50° C.

17. A continuous process according to claim 11 wherein the Bronsted acid catalyst is selected from the group consisting of phosphoric acid, sulfuric acid, methanesulfonic acid, benzenesulfonic acid, p-toluenesulfonic acid, naphthalenesulfonic acid, naphthalenedisulfonic acid and an insoluble acidic ion exchange resin.

18. A continuous process according to claim 14 wherein the product recovered from the contact zone comprises ethylidene diacetate.

* * * * *